United States Patent
Falcon et al.

(10) Patent No.: US 8,999,632 B2
(45) Date of Patent: Apr. 7, 2015

(54) METHOD FOR MEASURING ATR INHIBITION MEDIATED INCREASES IN DNA DAMAGE

(71) Applicants: Vertex Pharmaceuticals Incorporated, Cambridge, MA (US); University of Newcastle Upon Tyne, Newcastle Upon Tyne (GB)

(72) Inventors: Susanna Falcon, Newbury (GB); Philip Reaper, Shillingford (GB); John Pollard, Abingdon (GB); Nicola Curtin, Newcastle upon Tyne (GB); Fiona Middleton, South Gosforth (GB); Tao Chen, SuZhou (CN)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/045,373

(22) Filed: Oct. 3, 2013

(65) Prior Publication Data

US 2014/0134596 A1    May 15, 2014

Related U.S. Application Data

(60) Provisional application No. 61/709,384, filed on Oct. 4, 2012.

(51) Int. Cl.
*A01N 1/02* (2006.01)
*C12Q 1/48* (2006.01)
*G01N 33/50* (2006.01)
*G01N 33/68* (2006.01)

(52) U.S. Cl.
CPC ............ *G01N 33/5047* (2013.01); *G01N 33/68* (2013.01)

(58) Field of Classification Search
USPC ........................................ 435/2, 15
See application file for complete search history.

(56) References Cited

PUBLICATIONS

Kao et al. Inhibition of Gamma-H2AX After Ionizing Radiation As a Biological Surrogate of Impaired Upstream DNA Damage Signaling and Radiosensitivity; Journal of Cancer Molecules, vol. 5, No. 2 (2010) pp. 49-54.*
Buscemi, G., et al., "DNA Damage-Induced Cell Cycle Regulation of Novel Chk2 Phosphoresidues", Molecular and Cellular Biology, 26(21), (2006), pp. 7832-7845 (DOI: 10.1128/MCB.00534-06).
Chen, T., et al., "Targeting the S and G2 checkpoint to treat cancer", Drug Discovery Today, 17(5/6), (2012), pp. 194-202, (DOI: 10.1016/j.drudis.2011.12.009).
Chen, T., et al., "Development of a biomarker of ATR activity in surrogate human tissues", Newcastle University, Poster, Nov. 2012.
Middleton, F.K., and Curtin, N.J., "ATR as a Therapeutic Target", Cancer Drug Discovery and Development, 2013, Author's Proof.
Ward, I.M. and Chen, J., "Histone H2AX is phosphorylated in an ATR-dependent manner in response to replicational stress", The Journal of Biological Chemistry, 276(51), (2001), pp. 47759-47762.

* cited by examiner

*Primary Examiner* — Susan Hanley
*Assistant Examiner* — Paul Martin
(74) *Attorney, Agent, or Firm* — Rory C. Stewart

(57) ABSTRACT

The present relates to methods for detecting DNA damage in subjects treated with an ATR inhibitor. More specifically, this invention relates to a method for measuring changes in levels of $\gamma$H2AX and/or pChk1$^{Ser345}$ in, e.g., surrogate tissue cells, following ex vivo stimulation with a DNA damaging agent.

5 Claims, 11 Drawing Sheets

METHOD FOR MEASURING ATR INHIBITION MEDIATED INCREASES IN DNA DAMAGE

CROSS-REFERENCE TO RELATED APPLICATIONS

The present application claims the benefit of under 35 U.S.C. §119 U.S. Provisional Application No. 60/709,384, filed Oct. 4, 2012.

BACKGROUND OF THE INVENTION

Ataxia talangiectasia mutated and Rad-3 related (ATR) kinase is an enzyme involved in the DNA damage response (DDR). This signaling network acts to detect and orchestrate a cell's response to certain forms of DNA damage, most notably double strand breaks and replication stress. Following treatment with many types of DNA damaging drugs and ionizing radiation, cells are reliant on the DDR for survival. It has been shown that disruption of the DDR can increase cancer cell sensitivity to these DNA damaging agents and thus may improve patient responses to such therapies. Inhibition of ATR is one approach that can be taken to disrupt the DDR and it has been shown that inhibition of ATR can markedly increase cancer cell sensitivity to DNA damaging agents. To support the clinical progression of ATR inhibitors it is necessary to develop biomarkers that can measure the degree of ATR inhibition or the impact ATR inhibition has on cellular DNA damage.

SUMMARY OF INVENTION

This invention relates to methods for detecting DNA damage in subjects administered an ATR inhibitor. More specifically, this invention relates to a method for measuring changes in levels of phosphorylated H2AX (γH2AX) and/or phosphorylated Chk1 ($pChk1^{Ser345}$) in, e.g., surrogate tissue cells, following ex vivo stimulation with a DNA damaging agent.

Moreover, this invention relates to methods for detecting DNA damage in the blood of subjects treated with an ATR inhibitor. More specifically, this invention relates to a method of measuring increases in levels of γH2AX in CD3+ white blood cells from blood, stimulated ex vivo with a DNA damaging agent, by flow cytometry.

BRIEF DESCRIPTION OF THE DRAWINGS

The invention is herein described, by way of example only, with reference to the accompanying drawings.

DESCRIPTION OF THE INVENTION

Figure 1:
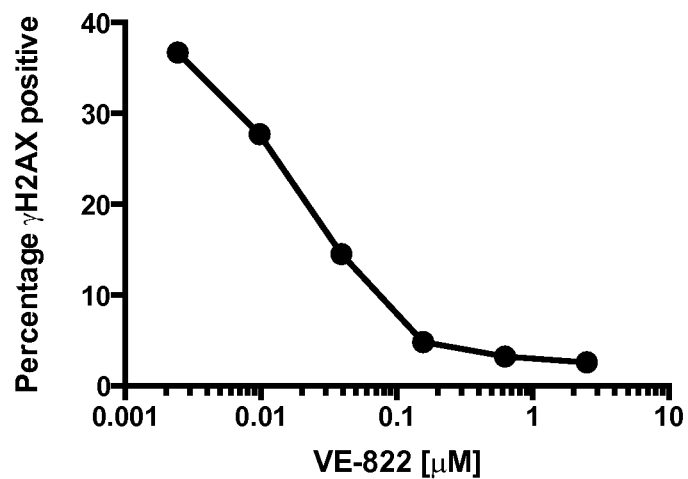
FIG. 1 depicts the level of γH2AX in purified human peripheral blood mononuclear cells (PBMCs) at varying doses of compound VE-822 using flow cytometry, following exposure to 4-nitroquinoline.

This invention provides a method for monitoring DNA damage in a subject by measuring changes in γH2AX and/or $pChk1^{Ser345}$, the method comprising:

a) administering an ATR inhibitor to a subject;

b) taking surrogate tissue cell samples from the subject at various intervals;

c) treating the surrogate tissue cell samples with a DNA damaging agent;

d) measuring γH2AX and/or $pChk1^{Ser345}$ levels in the cells by using antibodies specific for phospho-H2AX and/or $pChk1^{Ser345}$.

It shall be understood that "subject" includes patients, humans, and other animals, such as mice. In one embodiment, the subject is a non-human animal such as a mouse, rat, or dog. In a preferred embodiment, the subject is a human.

Any compound that inhibits ATR may be utilized when administering a compound to the subject. This may include those compounds that indirectly inhibit ATR via inhibition of an upstream or downstream target in the same biological pathway. In some embodiments, the ATR inhibitor does not need to be administered to the subject directly. Instead, surrogate tissue cell samples may be taken from the subject, and the ATR inhibitor may be administered directly to the surrogate tissue cell sample. Examples of ATR inhibitors that may be used include:

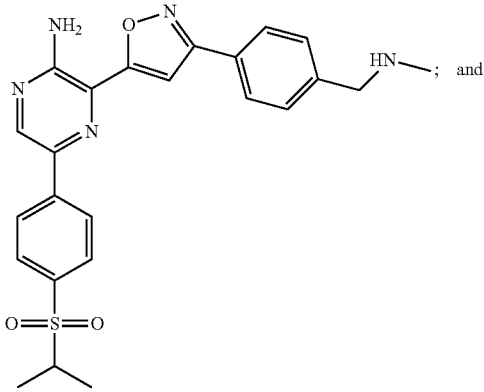

VE-822

VE-821

In some embodiments, the ATR inhibitor is:

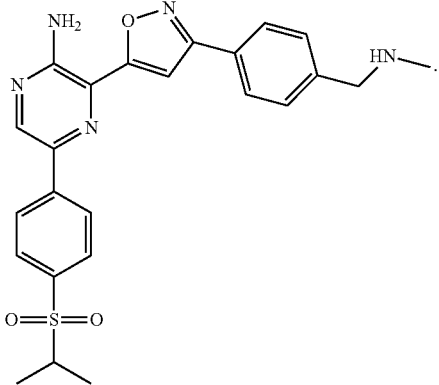

VE-822

Other examples of ATR inhibitors that may be utilized in the present invention may include those compounds described in WO 2013/071094; WO 2013/071093; WO 2013/071090; WO 2013/071088; WO 2013/049859; WO 2013/049719; WO 2013/049720; WO 2013/049722; WO 2013/071085; WO 2013/049726; WO 2012/178125; WO 2012/178124; WO 2012/178123; WO 2012/138938; WO 2012/138938; WO 2011/163527; WO 2011/143423; WO 2011/143426; WO 2011/143425; WO 2011/143422; WO 2011/143419; WO 2011/143399; WO 2010/054398; and WO 2010/071837.

Pharmaceutically Acceptable Salts, Solvates, Chlatrates, Prodrugs and other Derivatives The compounds described and referenced herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^{+}(C_{1-4}alkyl)_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases, which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like are examples of suitable base addition salts.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

The compounds described herein can also exist as pharmaceutically acceptable solvates (e.g., hydrates) and clathrates. As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders. A "pharmaceutically acceptable derivative or prodrug" includes any pharmaceutically acceptable ester, salt of an ester, or other derivative or salt thereof of a compound described herein which, upon administration to a recipient, is capable of providing, either directly or indirectly, a compound described herein or an inhibitorily active metabolite or residue thereof. Particularly favoured derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —$NO_2$, —ONO, or —$ONO_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

Pharmaceutical Compositions

The compounds described in the present application may also exist as pharmaceutically acceptable compositions that optionally comprise a pharmaceutically acceptable carrier, adjuvant or vehicle.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Modes of Administration and Dosage Forms

The compounds and pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. Alternatively, the dosing schedule of the compounds of the present invention may vary.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, a dosage of between 0.01-50 mg/kg body weight/dose of the inhibitor can be administered to a patient receiving these compounds.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Prior to administering the ATR inhibitor, a surrogate tissue sample may be taken to act as a control. Following compound administration to the subject, surrogate tissue samples may be taken at scheduled time intervals. Preferably, the time intervals vary between 5 minutes and 48 hours after compound administration. More preferably, the time intervals may vary between 5 minutes and 1 hour after compound administration.

As used herein, the term "surrogate tissue cells" refers to any non-cancerous tissue within the subject. Examples of surrogate tissue cells that could be utilized include, but are not limited to, hair follicle cells, skin cells, and peripheral blood mononuclear cells (PBMCs). Samples may be gathered using a variety of methods, e.g., via a skin swab, hair pluck, skin puncture, or intravenous bleed.

Each surrogate tissue sample may be treated with a DNA damaging agent. In some examples, the DNA damaging agent is selected from 4-nitroquinoline (4-NQO), UV, ionizing radiation, radiomimetic neocarzinostatin, a platinating agent, a Topo I inhibitor, a Topo II inhibitor, an antimetabolite, an alkylating agent, an alkyl sulphonates, an antimetabolite, or an antibiotic. In other embodiments, the DNA damaging agent is UV or 4-nitroquinoline. In still other embodiments, the DNA damaging agent is UV. In yet another embodiment, the DNA damaging agent is 4-nitroquinoline. The concentration of 4-nitroquinoline introduced into surrogate tissue may preferably be between about 20 µM and about 500 µM, more preferably between about 50 µM and about 350 µM, and even more preferably between about 60 µM and about 300 µM. In some embodiments, the concentration of 4-nitroquinoline is about 240 µM.

Examples of Platinating agents include Cisplatin, Oxaliplatin, Carboplatin, Nedaplatin, Satraplatin and other derivatives. Other platinating agents include Lobaplatin, and Triplatin. Other platinating agents include Tetranitrate, Picoplatin, Satraplatin, ProLindac and Aroplatin.

Examples of Topo I inhibitor include Camptothecin, Topotecan, irinotecan/SN38, rubitecan and other derivatives. Other Topo I inhibitors include Belotecan.

Examples of Topo II inhibitors include Etoposide, Daunorubicin, Doxorubicin, Aclarubicin, Epirubicin, Idarubicin, Amrubicin, Pirarubicin, Valrubicin, Zorubicin and Teniposide.

Examples of Antimetabolites include members of the Folic family, Purine family (purine antagonists), or Pyrimidine family (pyrimidine antagonists). Examples of the Folic family include methotrexate, pemetrexed and relatives; examples of the Purine family include Thioguanine, Fludarabine, Cladribine, 6-Mercaptopurine, and relatives; examples of the Pyrimidine family include Cytarabine, gemcitabine, 5-Fluorouracil (5FU) and relatives.

Some other specific examples of antimetabolites include Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, Azacitidine and Hydroxyurea.

Examples of alkylating agents include Nitrogen mustards, Triazenes, alkyl sulphonates, Procarbazine and Aziridines. Examples of Nitrogen mustards include Cyclophosphamide, Melphalan, Chlorambucil and relatives; examples of nitrosoureas include Carmustine; examples of triazenes include Dacarbazine and temozolomide; examples of alkyl sulphonates include Busulfan.

Other specific examples of alkylating agents include Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin and Plicamycin.

Examples of antibiotics include Mitomycin, Hydroxyurea; Anthracyclines, Anthracenediones, Streptomyces family. Examples of Anthracyclines include doxorubicin, daunorubicin, epirubicin and other derivatives; examples of Anthracenediones include Mitoxantrone and relatives; examples of Streptomyces family include Bleomycin, Mitomycin C, and actinomycin.

When using whole blood as the surrogate tissue, circulating mononuclear blood cells, such as T-lymphocytes (e.g., CD3+ white blood cells) and PBMCs, may be purified by simultaneously fixing the blood sample and lysing red blood cells within the blood sample. The blood sample may be fixed via, e.g., a 4% (w/v) paraformaldehyde solution. Preferably, the sample is fixed 1-3 hours after exposure to the DNA damaging agent. In some embodiments, the sample is fixed less than one hour after exposure to the DNA damaging agent when levels of pChk1$^{Ser345}$ are being measured. In other embodiments, the sample is fixed less than 3 hours after exposure to the DNA damaging agent when γH2AX is being measured. Circulating mononuclear blood cells are subsequently isolated via centrifugation. Once the cells of interest have been isolated, varying immunological techniques may be utilized to measure the levels of γH2AX and/or pChk1$^{Ser345}$, e.g., flow cytometry, western blotting, or immunofluorescence. To detect γH2AX and/or pChk1$^{Ser345}$, the proteins are tagged with antibodies, e.g., mouse monoclonal anti-phospho-H2AX$^{Ser139}$ antibody (available through, e.g., Millipore®) or rabbit monoclonal anti-pChk1$^{Ser345}$ antibody (available through, e.g., Cell Signaling Technologies®), respectively.

In some embodiments, the measurement of γH2AX and/or pChk1$^{Ser345}$ levels is done by flow cytometry. In another embodiment, the measurement of γH2AX and/or pChk1$^{Ser345}$ is done by immunofluorescence. In still other embodiments, the measurement of γH2AX and/or pChk1$^{Ser345}$ is done by western blot.

In some embodiments, the measurement of γH2AX and/or pChk1$^{Ser345}$ levels is performed in circulating mononuclear blood cells. In other embodiments, the measurement of γH2AX levels is performed in lymphocytes. In yet other embodiments, the measurement of γH2AX levels is performed in CD3+ white blood cells. In still other embodiments, the measurement of γH2AX levels is performed in peripheral blood mononuclear cells (PBMCs).

In another aspect of the present invention, a method for monitoring DNA damage in a subject by measuring accumulation of γH2AX from blood is provided, the method comprising:

a) treating a subject with an ATR inhibitor;
  b) taking blood samples from the subject at various intervals;

c) treating the blood samples with a DNA damaging agent;
d) isolating white blood cells from the blood samples; and
e) measuring phospho-H2AX levels in the white blood cells by using antibodies specific for γH2AX.

In some embodiments, the DNA damaging agent is 4-nitroquinoline. In other embodiments, the DNA damaging agent is UV.

In yet other embodiments, the white blood cells are purified by simultaneously fixing the blood sample and lysing red blood cells within the blood sample, followed by centrifugation. In other examples, the sample is fixed 1-3 hours after exposure to a DNA damaging agent. In yet another embodiment, the sample is fixed less than 3 hours after exposure to the DNA damaging agent when measuring γH2AX.

In some embodiments, the measurement of γH2AX levels is done by flow cytometry. In another embodiment, the measurement of γH2AX is done by immunofluorescence. In still other embodiments, the measurement of γH2AX is done by western blot.

In another embodiment, the measurement of γH2AX levels is performed in surrogate tissue. In some embodiments, the measurement of γH2AX levels is performed in circulating mononuclear blood cells. In other embodiments, the measurement of γH2AX levels is performed in lymphocytes. In yet other embodiments, the measurement of γH2AX levels is performed in CD3+ white blood cells. In still other embodiments, the measurement of γH2AX levels is performed in PBMCs.

In some embodiments, the ATR inhibitor is selected from:

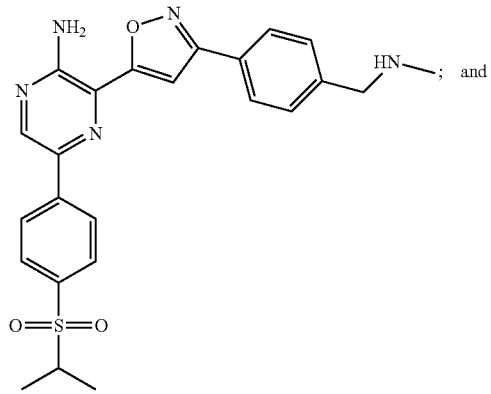

VE-822

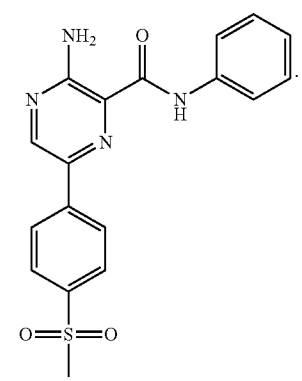

VE-821

In some embodiments, the ATR inhibitor is:

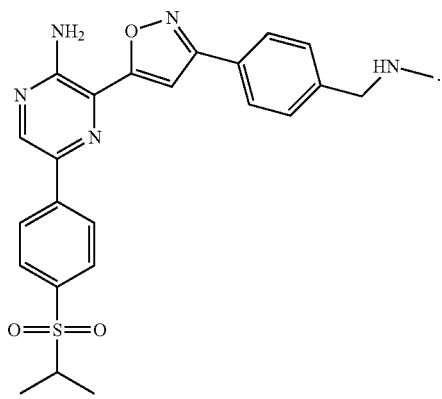

VE-822

Experimental Design

A method for stimulating and analysing ATR activity in non-cycling cells was first established in purified PBMCs then the method was adapted to enable stimulation and analysis of ATR activity in white blood cell populations in whole human and murine blood. ATR activity was stimulated with 4-nitroquinoline or UV and monitored by measuring H2AX and/or Chk1 phosphorylation. Dose-dependent inhibition of this activity by an ATR inhibitor, i.e., compound VE-822 or compound VE-821, was confirmed.

Methods and Data i) Analysis of ATR Inhibition of Compound VE-822 in Purified Human PBMCs via Flow Cytometry PBMCs were purified from fresh whole human blood using Ficoll paque density gradient centrifugation. Cells were counted and seeded at 5×10(5) per well in a round bottom 96 well plate in RPMI medium supplemented with 10% foetal calf serum (FCS) and penicillin/streptomycin/glutamine (PSQ). The cells were pre-incubated with compound VE-822 for 10 min at 37° C., stimulated with 1.5 uM 4-nitroquinoline (4-NQO) for 1 h at 37° C. Washed cells were then fixed with 4% paraformaldehyde for 10 min, permeabilised with 0.5% Triton X-100 for 10 min and analysed for Histone H2AX S139 phosphorylation by flow cytometry on the using 1:200 diluted anti-γH2AX primary antibody clone JBW301 (Millipore), 1:500 goat anti-mouse Alexa Fluor488 (Invitrogen) and propidium iodide DNA staining.

Referring to FIG. 1, compound VE-822 dose-dependently inhibits 4-nitroquinoline stimulated H2AX phosphorylation in purified human PBMCs. An IC50 of 20 nM was determined. As stated above, this method was adapted to enable stimulation and analysis of ATR activity in white blood cell populations in whole human and murine blood.

ii) Analysis of ATR Inhibition of Compound VE-822 in Whole Human and Murine Blood ex vivo via Flow Cytometry Whole human or mouse blood was collected in heparinised tubes and 1-2 h later 1 ml (human) or 500 ul (mouse) was dispensed into 50 or 15 ml falcon tubes pre-spiked with compound VE-822. The samples were mixed by agitation, incubated for 10 min at 37° C. and stimulated with 62 uM (human) or 124 uM (mouse) 4-nitroquinoline for 1 h at 37° C. The samples were then fixed and red blood cells were lysed using Lyse/Fix Buffer (BD) for 5-10 min and white blood cells were collected by centrifugation according to the manufacturer's instructions. The samples were then transferred into 96 well round bottom plates and permeabilised using Triton X-100 according to method i). H2AX phosphorylation was then analysed by flow cytometry according to method i) with selection of lymphocytes using either standard scatterplot gating or CD3 staining. For specific analysis of H2AX phosphorylation in CD3 positive lymphocytes, cells were stained with 1:2.5 diluted PE-conjugated anti-human CD3 (BD) (human) and 1:50 diluted APC-conjugated anti-mouse CD3 (BD) (mouse) in place of propidium iodide and analyses of P-H2AX were performed on the CD3-positive population.

Figure 2:
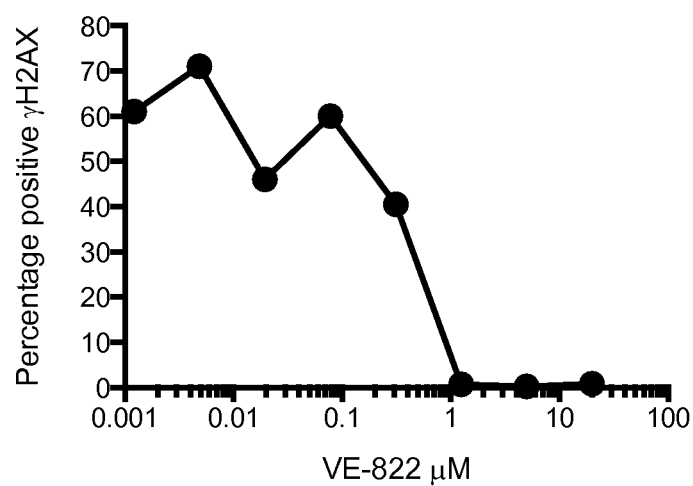
FIG. 2 depicts the level of γH2AX in lymphocytes in whole human blood at varying doses of compound VE-822 using flow cytometry (scatterplot gating), following exposure to 4-nitroquinoline ex vivo.
Figure 3:
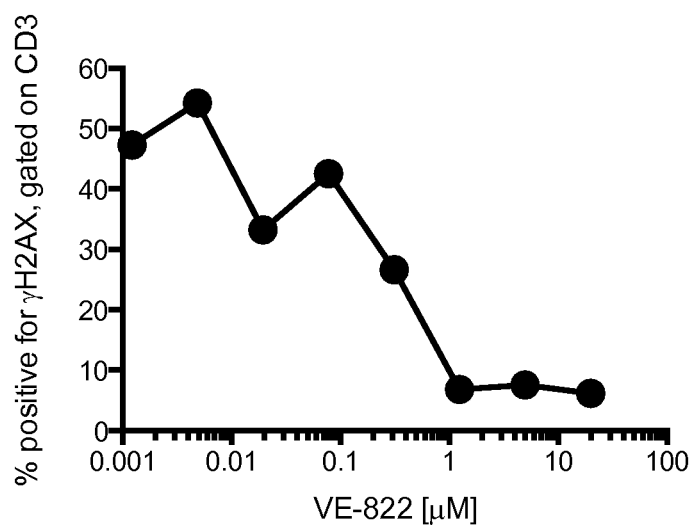
FIG. 3 depicts the level of γH2AX in lymphocytes in whole human blood at varying doses of VE-822 using flow cytometry (gating on CD3+ cells), following exposure to 4-nitroquinoline ex vivo.
Figure 4:
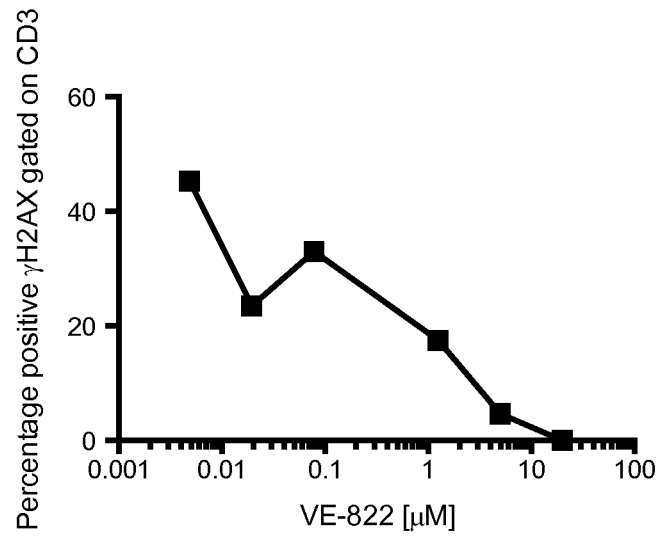
FIG. 4 depicts the level of γH2AX in lymphocytes in whole mouse blood at varying doses of VE-822 using flow cytometry (gating on CD3+ cells), following exposure to 4-nitroquinoline ex vivo.

Dose-dependent inhibition of this activity by compound VE-822 was again confirmed. Compound VE-822 dose-dependently inhibits 4-nitroquinoline stimulated H2AX phosphorylation in lymphocytes in whole human (FIGS. 2 and 3) or mouse (FIG. 4) blood ex vivo. Lymphocytes were analysed through either scatterplot gating or CD3+ staining. IC50s of 0.6 uM and 1 uM were determined in human and mouse blood, respectively.

iii) Analysis of ATR Inhibition of Compound VE-821 in PBMCs from Human Whole Blood via Western Blot Blood from healthy volunteers was collected by venepuncture into EDTA-coated blood collection tubes. 6 mls of blood was diluted 1:1 in PBS and transferred into 50 ml falcon tubes containing 6 mls Ficoll-Paque Plus (GE Healthcare). PBMCs were separated using centrifugation through a Ficoll-Paque Plus separation gradient. PBMCs were collected and washed twice with 20 mls PBS before being resuspended in 6 mls culture medium (RPMI-1640 with 10% FBS). 2 mls of PBMC suspension were transferred into one well of a 6-well culture dish. Following 1 hour's incubation at 37° C. with 5% $CO_2$, PBMCs were exposed to 10 $J/m^2$ 254 nm UV (UV) treatment (where indicated) using a Stratalinker-2400 (Stratagene) and incubated for a further 2 or 24 hours. Control cells were not exposed to UV. PBMCs were collected by centrifugation and washed in PBS, before being lysed by resuspension in approximately 40 µl Phosphosafe Extraction Reagent (EMD Millipore), vortexed and incubated at room temperature for 10 minutes. Protein concentration in lysates was determined using a Pierce protein assay (Thermo). 20 µg of protein was loaded and proteins were separated using gel electrophoresis using a 4-15% Tris Glycine gel (BioRad) and run in Tris-glycine SDS running buffer (192 mM glycine, 25 mM Tris-base, 1% (w/v) SDS) at 200V for 30 minutes. Proteins were transferred onto nitrocellulose membrane (Hybond-C Extra, GE Healthcare) using BioRad western blotting apparatus in Tris-Glycine transfer buffer (192 mM Glycine, 25 mM Tris, 20% (v/v) methanol) at 100 v for 1 hour. After blocking with 5% BSA (w/v) in TBST (20 mM Tris base, 137 mM NaCl, 0.01% (v/v) Tween 20) for 60 minutes at room temperature, proteins of interest were detected following overnight incubation at 4° C. with the following primary antibodies in BSA diluted in TBST: goat anti-ATR antibody (N-19, Santa Cruz Biotechnology, Dallas, Tex., USA. 1:300 in 1% (w/v) BSA), mouse anti-PARP (3001-100, BioVision 1:1000-in 1% (w/v) BSA), rabbit anti-pChk1$^{Ser345}$ (133D3, Cell Signaling Technology, 1:1000 in 5% (w/v) BSA) and mouse anti-actin (Sigma, 1:1000 in 1% (w/v) BSA). These were detected by 1 hour incubation at room temperature with the appropriate secondary antibodies diluted in 1% (w/v) BSA in TBST: anti-goat HRP (Cell Signaling Technology 1:2000), anti-mouse HRP (Dako, 1:2000) or anti-rabbit HRP (Dako, 1:1000) as appropriate. Membranes were washed in 10 mls TBST for 3×10 minutes between antibodies. Chemiluminescence was detected using G-box equipment (Syngene) following development using ECL-Prime (GE Healthcare). Protein bands were quantified using densitometry using Genetools software (Syngene) and analysis performed using GraphPad Prism version 6.0.

Figure 5:
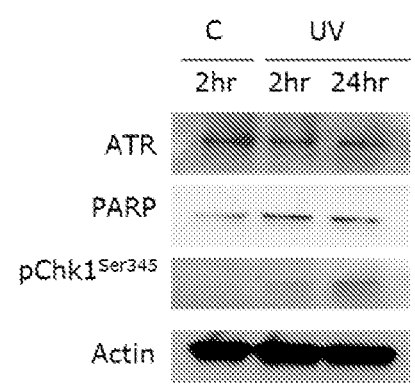
FIG. 5 depicts a western blot of ATR, PARP, $pChk1^{Ser345}$, and Actin in PBMCs following exposure to UV.

Referring to FIG. 5, pChk1$^{Ser345}$ signals were detectable by western blotting isolated PBMCs exposed to UV for 2 and 24 hr. PARP and actin were used as loading controls and ATR levels were not significantly changed. Therefore, Western Blot analysis is a viable option for detecting pChk1$^{Ser345}$ in PBMCs following UV administration.

iv) Analysis of ATR Inhibition of Compound VE-821 in Purified PBMCs from Human Whole Blood after Treatment with DNA Damaging Agents Using Immunofluorescence.

Blood from healthy volunteers was collected by venepuncture into EDTA-coated blood collection tubes. 2×10 ml aliquots of blood was diluted 1:1 in PBS and transferred into 50 ml falcon tubes containing 10 mls Ficoll-Paque Plus (GE Healthcare). PBMCs were separated using centrifugation through a Ficoll-Paque Plus separation gradient. PBMCs from each tube were collected separately and washed twice with 20 mls PBS before being pooled and resuspended in 20 mls culture medium (RPMI-1640 with 10% FBS). 2 mls of PBMC suspension per treatment were transferred into one well of a 6-well culture dish. Following 1 hour's incubation at 37° C. with 5% $CO_2$, PBMCs collected separately, centrifuged and were resuspended in culture medium containing hydroxyurea (HU, 10 mM) or 4-nitroquinoline (2.5 µM) as indicated with or without 10 µM of compound VE-821 (Vertex Pharmaceuticals). Controls remained in drug-free medium +/−10 µM of compound VE-821. After 1 hour, where appropriate, PBMCs in as yet untreated or compound VE-821-containing medium were exposed to 50 $J/m^2$ 254 nm UV (UV) using a Stratalinker-2400 (Stratagene) then incubated for a further hour. PBMCs were collected using centrifugation, washed in 1 ml PBS then resuspended in 1 ml PBS before being counted using a haemocytometer. 1×10$^5$ PBMCs were centrifuged onto microscope slides using a Cytospin 2 centrifuge (Shandon) for 5 minutes at 450 rpm. Cells were fixed using 4% (w/v) paraformaldehyde for 20 minutes and permeablised using 0.5% (v/v) Triton-X-100 for 30 minutes. Permeablised cells were blocked using 10% (v/v) goat serum and 5% (w/v) BSA in PBS for 1 hour, and subjected to immunofluorescent analysis using primary antibodies diluted in 1% (w/v) BSA in PBS overnight at 4° C.: rabbit anti-pChk1$^{Ser345}$ (133D3, Cell Signaling Technology, 1:300) and mouse anti-phospho-Histone H2AX Ser139 (JBW301, Millipore, 1:1000). These were detected using the appropriate secondary antibodies diluted in 1% (w/v) BSA in PBS for 1 hour at room temperature protected from the light: anti-rabbit AlexaFluor 488 (Invitrogen, 1:1000) and anti-mouse AlexaFluor 546 (Invitrogen, 1:1000). DNA was stained using Vectashield with DAPI (Vector Laboratories). Images were captured using a Zeiss LSM 700 confocal microscope (Zeiss) with Zen 2009 software (Zeiss) using a ×40 lens and wavelengths of 405 nm, 488 nm and 561 nm. Mean nuclear fluorescence for at least 50 nuclei was measured using ImageJ software (National Institutes of Health, USA) and the data analysed using GraphPad Prism software version 6.0.

Figure 6:
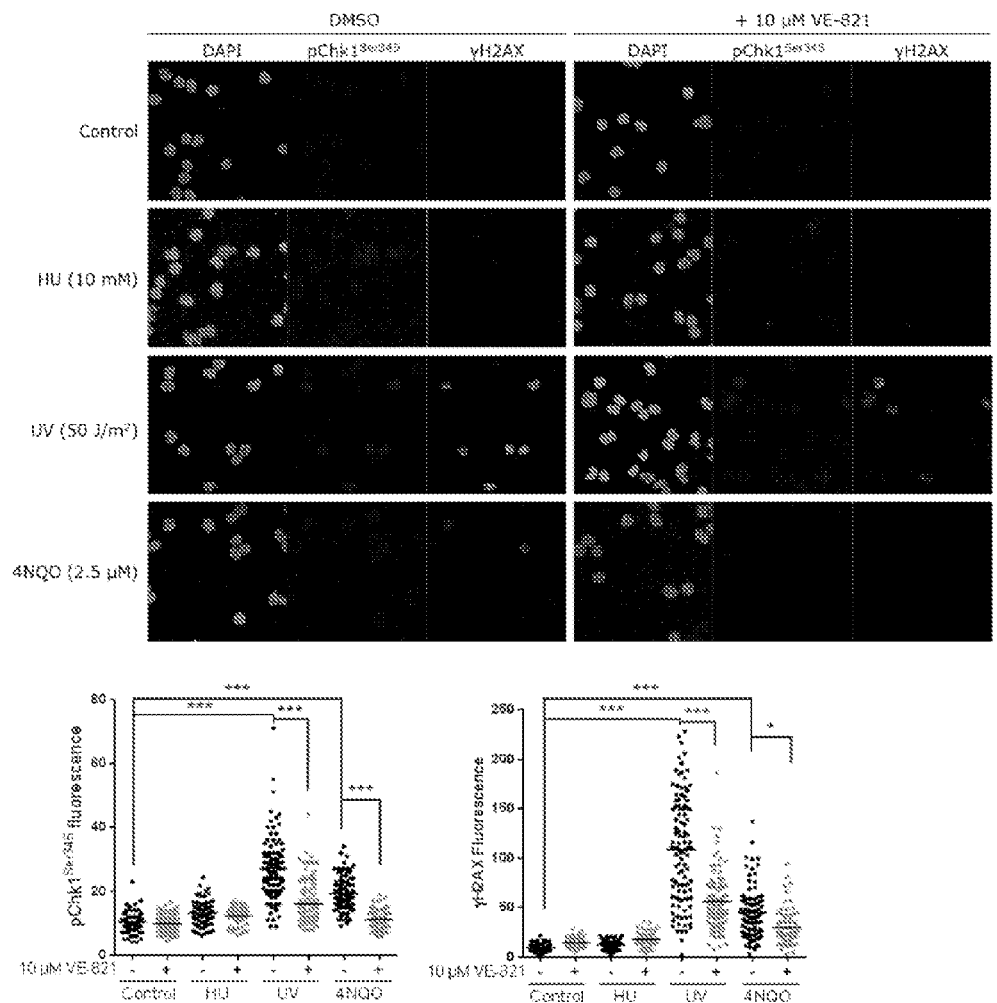
FIG. 6 depicts the levels of γH2AX and $pChk1^{Ser345}$ in purified PBMCs, after treatment with DNA damaging agents and VE-821 using immunofluorescence.

Referring to FIG. 6, signals for γH2AX and pChk1$^{Ser345}$ were evident in purified PBMCs using immunofluorescence upon exposure to UV or 4-nitroquinoline at the concentrations/doses and times indicated. After co-administering compound VE-821, a reduction in the level of pChk1$^{Ser345}$ and γH2AX signals was observed.

v) Analysis of ATR Inhibition of Compound VE-821 in PBMCs after Treatment of Human Whole Blood with DNA Damaging Agents Using Immunofluorescence.

Blood from healthy volunteers was collected by venepuncture into EDTA-coated blood collection tubes. 2 mls of blood per treatment was transferred into 1 well of a 6-well plates already containing 2 mls PBS containing 2% (v/v) FBS and DMSO or compound VE-821 (10 µM final concentration). Following 1 hour incubation at 37° C. and 5% CO2, blood was exposed to 50 $J/m^2$ UV light. Following 1 hour further incubation the blood mixture was transferred into 15 ml falcon tubes containing 2 mls Ficoll-Paque Plus and the PBMCs separated using centrifugation through a Ficoll-Paque Plus separation gradient. PBMCs were collected and washed twice using 10 mls PBS and resuspended in 1 ml PBS. PBMCs were counted using a haemocytometer and 1×10$^5$ PBMCs were centrifuged onto microscope slides using a Cytospin 2 centrifuge (Shandon) for 5 minutes at 450 rpm. Cells were fixed using 4% (w/v) paraformaldehyde for 20 minutes and permeablised using 0.5% (v/v) Triton-X-100 for 30 minutes. Permeablised cells were blocked using 10% (v/v) goat serum and 5% (w/v) BSA in PBS for 1 hour, and subjected to immunofluorescent analysis using primary antibodies diluted in 1% (w/v) BSA in PBS at 4° C. overnight: rabbit anti-pP (133D3, Cell Signaling Technology, 1:300) and mouse anti-phospho-Histone H2AX$^{Ser139}$ (JBW301, Millipore, 1:1000). These were detected using the appropriate secondary antibodies diluted in 1% (w/v) BSA in PBS for 1 hour at room temperature protected from the light: anti-rabbit AlexaFluor 488 (Invitrogen, 1:1000) and anti-mouse AlexaFluor 546 (Invitrogen, 1:1000). DNA was stained using Vectashield with DAPI (Vector Laboratories). Images were captured using a Zeiss LSM 700 confocal microscope (Zeiss) with Zen 2009 software (Zeiss) using a ×40 lens and wavelengths of 405 nm, 488 nm and 561 nm. Mean nuclear fluorescence for at least 50 nuclei was measured using ImageJ software (National Institutes of Health, USA) and the data analysed using GraphPad Prism software version 6.0.

Figure 7:
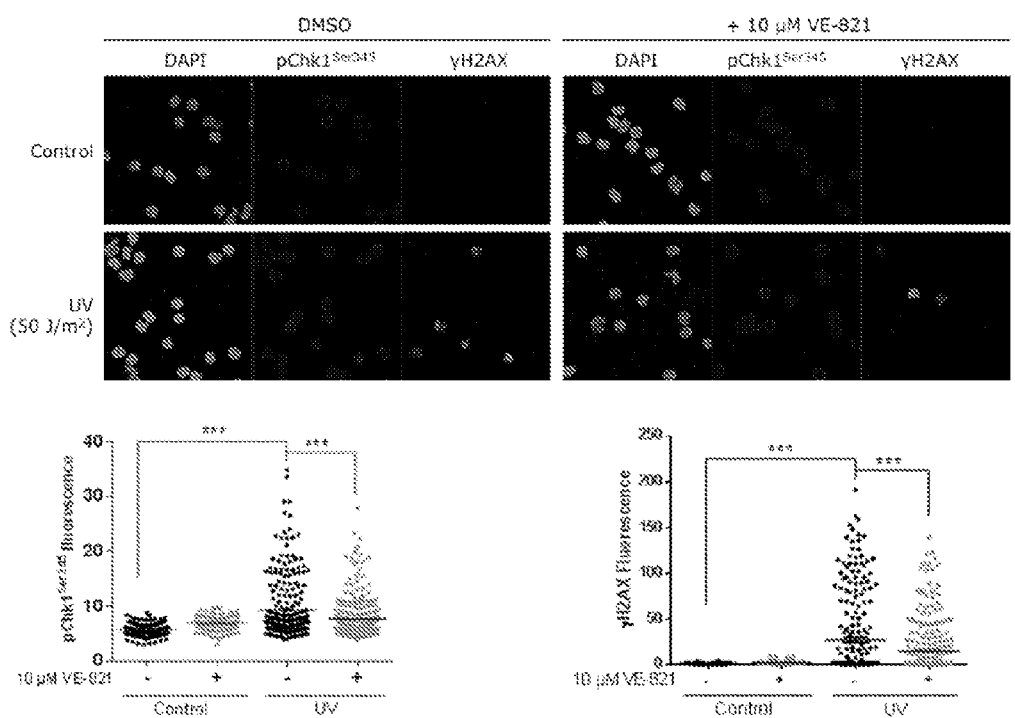
FIG. 7 depicts the levels of γH2AX and $pChk1^{Ser345}$ in PBMCs after treatment of human whole blood with a DNA damaging agents and VE-821 using immunofluorescence.

Referring to FIG. 7, analysis of the PBMCs by immunofluorescence microscopy revealed that UV caused a significant increase in pChk1$^{Ser345}$ and γH2AX. After co-administration of VE-821, there was significant inhibition of pChk1$^{Ser345}$ and γH2AX. Accordingly, immunofluorescence is a viable option for analysing PBMCs, purified after the administration of a DNA damaging agent, to determine whether ATR inhibition is occurring in a subject.

vi) Analysis of ATR Inhibition of Compound VE-822 in PBMCs after Treatment of Human Whole Blood with 4-Nitroquinoline Using Immunofluorescence Blood from healthy volunteers was collected by venepuncture into EDTA-coated blood collection tubes. 2 mls of blood per treatment was transferred into 1 well of a 6-well plates already containing 2 mls PBS containing 2% (v/v) FBS and DMSO or 4-nitroquinoline (240 μM final concentration) with or without compound VE-821 as indicated (1 or 10 μM final concentration). Following 1 or 2 hours incubation (as indicated) at 37° C. the blood mixture was transferred into 15 ml falcon tubes containing 2 mls Ficoll-Paque Plus and the PBMCs separated using centrifugation through a Ficoll-Paque Plus separation gradient. PBMCs were collected and washed twice using 10 mls PBS and resuspended in 1 ml PBS. PBMCs were counted using a haemocytometer and 1×10$^5$ PBMCs were centrifuged onto microscope slides using a Cytospin 2 centrifuge (Shandon) for 5 minutes at 450 rpm. Cells were fixed using 4% (w/v) paraformaldehyde for 20 minutes and permeablised using 0.5% (v/v) Triton-X-100 for 30 minutes. Permeablised cells were blocked using 10% (v/v) goat serum and 5% (w/v) BSA in PBS for 1 hour, and subjected to immunofluorescent analysis using primary antibodies diluted in 1% (w/v) BSA in PBS: rabbit anti-pChk1$^{Ser345}$ (133D3, Cell Signaling Technology, 1:300) and mouse anti-phospho-Histone H2AX$^{Ser139}$ (JBW301, Millipore, 1:1000). These detected using the appropriate secondary antibodies diluted in 1% (w/v) BSA in PBS: anti-rabbit AlexaFluor 546 (Invitrogen, 1:1000) and anti-mouse AlexaFluor 546 (Invitrogen, 1:1000). DNA was stained using Vectashield with DAPI (Vector Laboratories). Images were captured using a Zeiss LSM 700 confocal microscope (Zeiss) with Zen 2009 software (Zeiss) using wavelengths of 405 nm and 561 nm. Mean nuclear fluorescence for at least 50 nuclei was measured using Image) software (National Institutes of Health, USA) and the data analysed using GraphPad Prism software version 6.0.

Figure 8:
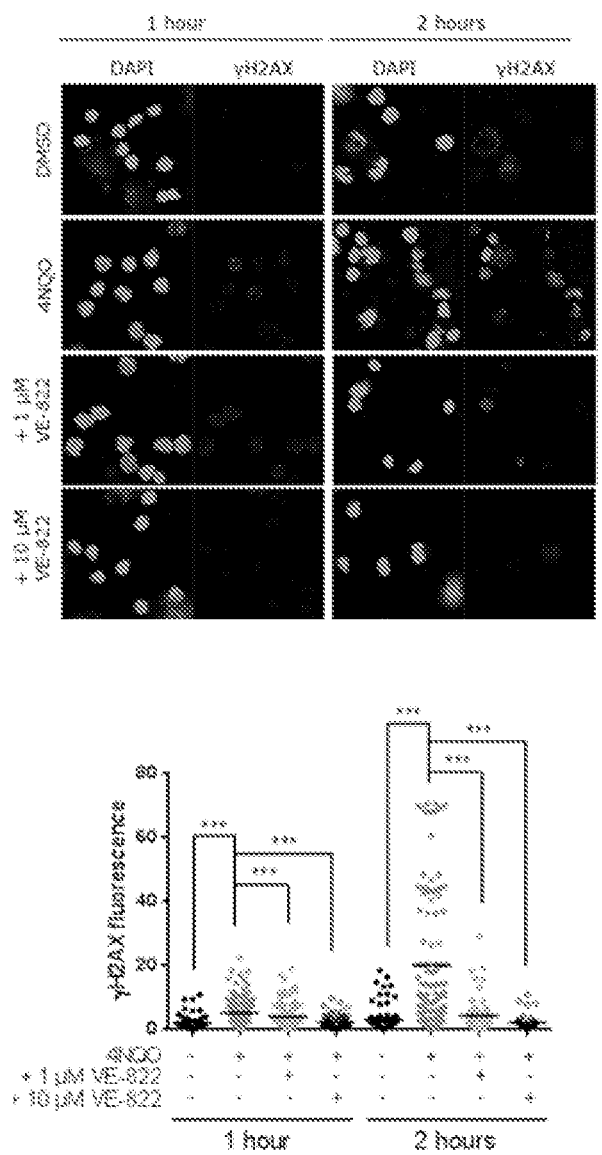
FIG. 8 depicts the levels of γH2AX and $pChk1^{Ser345}$ in PBMCs after treatment of human whole blood with 4-nitroquinoline and VE-822 using immunofluorescence.

Referring to FIG. 8, 4-nitroquinoline caused an increase in γH2AX at both 1 and 2 hr. Increases in γH2AX were inhibited by VE-822 in a concentration-dependent manner. These results provide confirmation of the results shown in FIG. 7, discussed above, thus supporting the use of the described method for determining ATR inhibition in a subject using surrogate tissue.

vii) Evaluation of Optimal 4-Nitroquinoline Concentration in PBMCs

Blood from healthy volunteers was collected by venepuncture into EDTA-coated blood collection tubes. 2 mls of blood per treatment was transferred into 1 well of a 6-well plates already containing 2 mls PBS containing 2% (v/v) FBS and DMSO or 4-nitroquinoline (60, 120, 240, 480 μM final concentration). Following 2 hours incubation at 37° C. the blood mixture was transferred into 15 ml falcon tubes containing 2 mls Ficoll-Paque Plus and the PBMCs separated using centrifugation through a Ficoll-Paque Plus separation gradient. PBMCs were collected and washed twice using 10 mls PBS and resuspended in 1 ml PBS. PBMCs were counted using a haemocytometer and 1×10$^5$ PBMCs were centrifuged onto microscope slides using a Cytospin 2 centrifuge (Shandon) for 5 minutes at 450 rpm. Cells were fixed using 4% (w/v) paraformaldehyde for 20 minutes and permeablised using 0.5% (v/v) Triton-X-100 for 30 minutes. Permeablised cells were blocked using 10% (v/v) goat serum and 5% (w/v) BSA in PBS for 1 hour, and subjected to immunofluorescent analysis using primary antibodies diluted in 1% (w/v) BSA in PBS: rabbit anti-pChk1$^{Ser345}$ (133D3, Cell Signaling Technology, 1:300) and mouse anti-phospho-Histone H2AX$^{Ser139}$ (JBW301, Millipore, 1:1000). These were detected using the appropriate secondary antibodies diluted in 1% (w/v) BSA in PBS: anti-rabbit AlexaFluor 546 (Invitrogen, 1:1000) and anti-mouse AlexaFluor 546 (Invitrogen, 1:1000). DNA was stained using Vectashield with DAPI (Vector Laboratories). Images were captured using a Zeiss LSM 700 confocal microscope (Zeiss) with Zen 2009 software (Zeiss) using wavelengths of 405 nm and 561 nm. Mean nuclear fluorescence for at least 50 nuclei was measured using Image) software (National Institutes of Health, USA) and the data analysed using GraphPad Prism software version 6.0.

Figure 9:
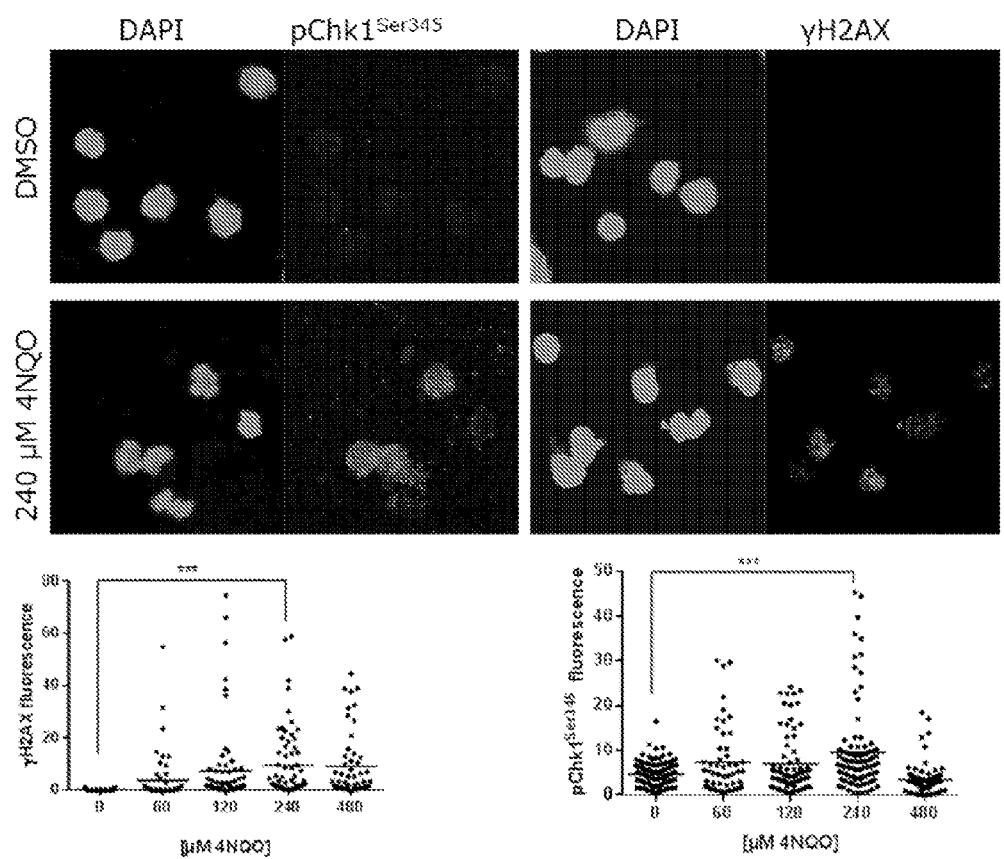
FIG. 9 depicts the levels of γH2AX and $pChk1^{Ser345}$ in PBMCs after treatment of human whole blood with 4-nitroquinoline at varying doses.

Referring to FIG. 9, the concentration of 4-nitroquinoline was evaluated for biomarker induction by treating whole blood with varying concentrations of 4-nitroquinoline. Data are representative immunofluorescent images of cells treated with DMSO or 240 μM 4-nitroquinoline, and quantitation of dose-response to 4-nitroquinoline. In cell lines and in isolated PBMCs ≤5 μM 4-nitroquinoline was adequate to induce ATR-dependent phosphorylation events. However, 4-nitroquinoline concentrations at 240 μM provided improved phosphorylation of pChk1$^{Ser345}$ and γH2AX.

viii) Evaluation of Optimal 4-Nitroquinoline Concentration in MCF7 Cells

Coverslips were sterilised in methanol and placed in the bottom of a 6-well culture dish. 2×10$^5$ MCF7 cells were seeded into each well of a 6-well culture dish in culture medium (RPMI-1640 with 10% FBS and 1% penicillin and streptomycin) and allowed to adhere for 24 hours. Medium was replaced by fresh medium containing 4-nitroquinoline (0.1-10 μM) and incubated at 37° C. for 2 hours. Cells were washed in PBS, fixed using 4% (w/v) paraformaldehyde for 20 minutes at room temperature and permeablised using 0.5% (v/v) Triton-X-100 for 30 minutes at room temperature. Permeablised cells were blocked using 10% (v/v) goat serum and 5% (w/v) BSA in PBS for 1 hour, the coverslips removed and subjected to immunofluorescent analysis using primary antibodies diluted in 1% (w/v) BSA in PBS overnight at 4° C.: rabbit anti-pChk1$^{Ser345}$ (133D3, Cell Signaling Technology, 1:300) and mouse anti-phospho-Histone H2AX$^{Ser139}$ (JBW301, Millipore, 1:1000). These were detected using the appropriate secondary antibodies diluted in 1% (w/v) BSA in PBS for 1 hour at room temperature protected from light: anti-rabbit AlexaFluor 546 (Invitrogen, 1:1000) and anti-mouse AlexaFluor 546 (Invitrogen, 1:1000). Coverslips were washed three times for 10 minutes in PBS between antibodies. DNA was stained using Vectashield with DAPI (Vector Laboratories). Images were captured using a Zeiss LSM 700 confocal microscope (Zeiss) with Zen 2009 software (Zeiss) using and ×40 lens and wavelengths of 405 nm and 561 nm. Mean nuclear fluorescence for at least 50 nuclei was measured using Image) software (National Institutes of Health, USA) and the data analysed using GraphPad Prism software version 6.0.

Figure 10:
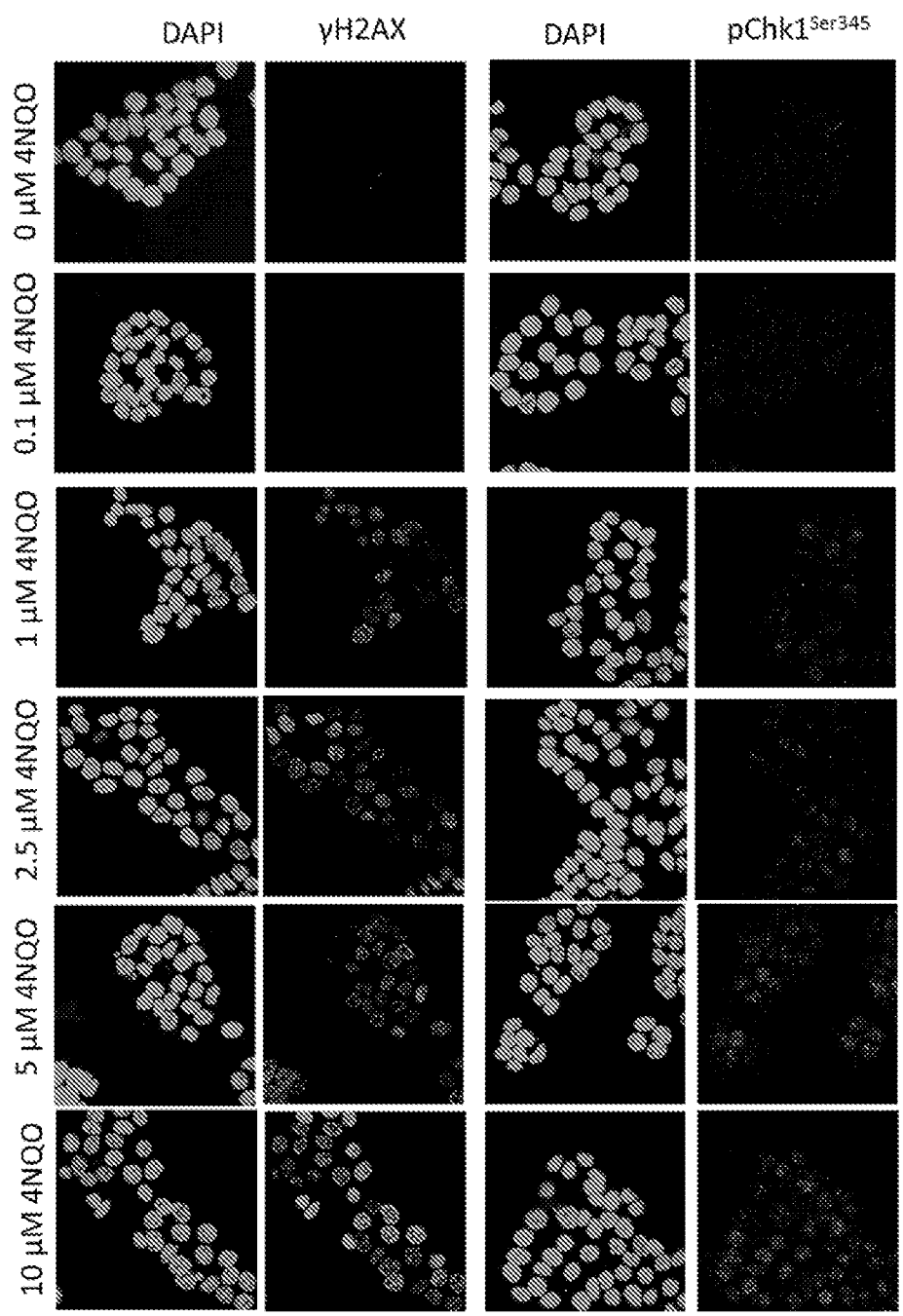
FIG. 10 depicts $pChk1^{Ser345}$ and γH2AX levels in MCF7 cells treated with varying concentrations of 4-nitroquinoline using immunofluorescence.

Referring to FIG. 10, an experiment analogous to the one described in section vii), above, was conducted. As shown in FIG. 10, lower concentrations were required in MCF7 cells to achieve a similar effect using 4-nitroquinoline as observed in whole blood.

ix) Evaluation of 4-Nitroquinoline Induced Phosphorylation of Chk1 and γH2AX over Various Time Intervals Following Treatment with Inhibitors of ATR, DNA-PK, and/or ATM Coverslips were sterilised in methanol and placed in the bottom of a 6-well culture dish. 2×10$^5$ MCF7 cells were seeded into each well of a 6-well culture dish in culture medium (RPMI-1640 with 10% FBS and 1% penicillin and streptomycin) and allowed to adhere for 24 hours. Medium was replaced by fresh medium containing compound VE-821 (10 µM) and incubated at 37° C. for minutes where appropriate. Medium was then replaced (where appropriate) with medium containing 4-nitroquinoline (2.5 µM) with or without compound VE-821 (10 µM) or KU55933 and NU7441 (10 µM and 1 µM, respectively). Cells were incubated at 37° C. for 0.5, 1 and 3 hours at which points they were washed with 2 mls PBS and fixed. Cells were fixed using 4% (w/v) paraformaldehyde for minutes at room temperature and permeablised using 0.5% (v/v) Triton-X-100 for 30 minutes at room temperature. Permeablised cells were blocked using 10% (v/v) goat serum and 5% (w/v) BSA in PBS for 1 hour at room temperature, the coverslips removed and subjected to immunofluorescent analysis using primary antibodies diluted in 1% (w/v) BSA in PBS overnight at 4° C.: rabbit anti-pChk1$^{Ser345}$ (133D3, Cell Signaling Technology, 1:300) and mouse anti-phospho-Histone H2AX$^{Ser139}$ (JBW301, Millipore, 1:1000). These were detected using the appropriate secondary antibodies diluted in 1% (w/v) BSA in PBS for 1 hour at room temperature protected from light: anti-rabbit AlexaFluor 546 (Invitrogen, 1:1000) or anti-mouse AlexaFluor 546 (Invitrogen, 1:1000). Coverslips were washed three times for 10 minutes in PBS after incubation with each antibody. DNA was stained using Vectashield with DAPI (Vector Laboratories). Images were captured using a Zeiss LSM 700 confocal microscope (Zeiss) with Zen 2009 software (Zeiss) using and ×40 lens and wavelengths of 405 nm and 561 nm. Mean nuclear fluorescence for at least 50 nuclei was measured using Image) software (National Institutes of Health, USA) and the data analysed using GraphPad Prism software version 6.0.

Figure 11:
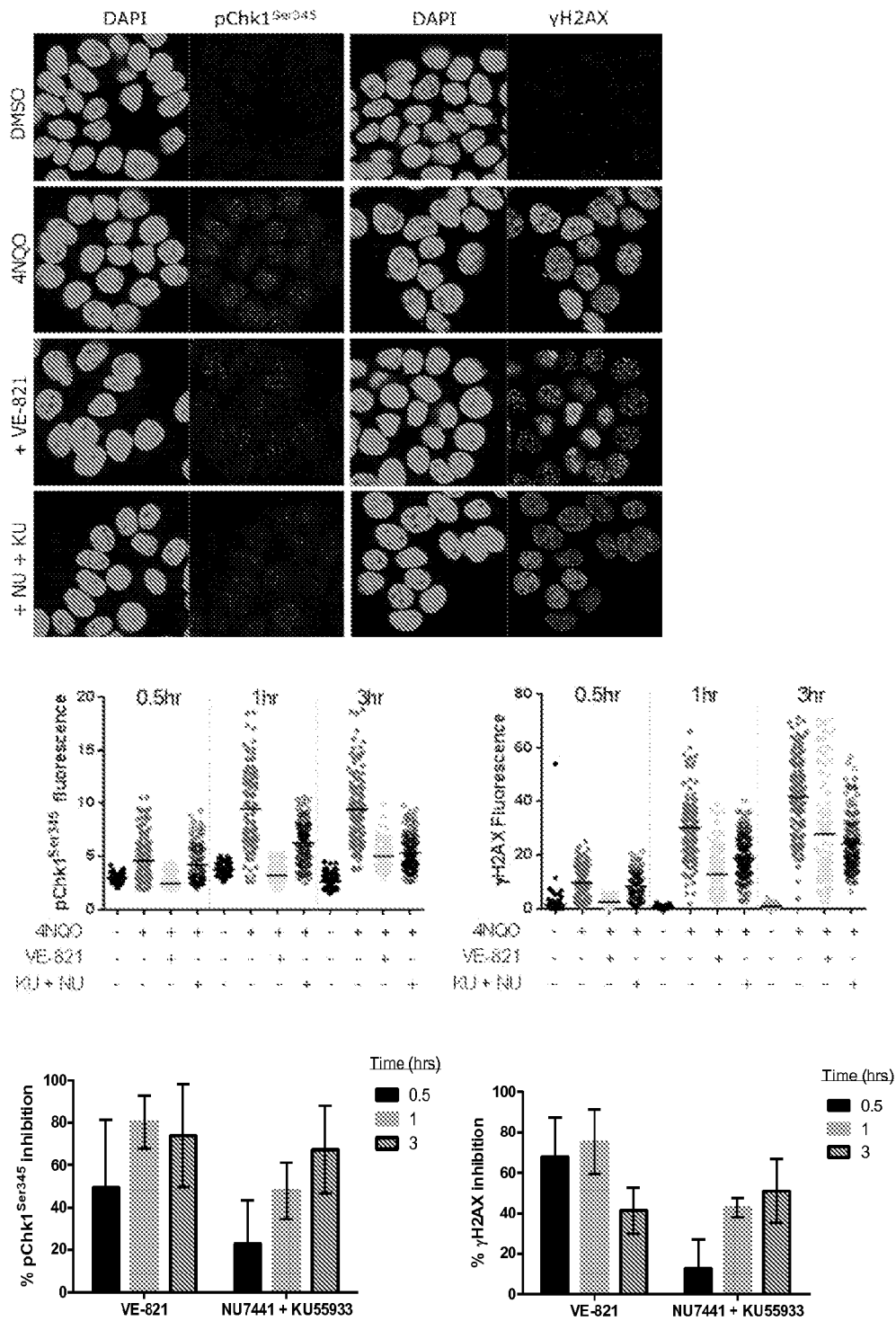
FIG. 11 depicts the levels of $pChk1^{Ser345}$ and γH2AX in MCF7 cells treated with 4-nitroquinoline and VE-821 (ATR inhibitor) or KU55933 (ATM inhibitor) and NU7441 (DNA-PK inhibitor) for varying time intervals using immunofluorescence.

Referring to FIG. 11, treatment of MCF7 cells with 4-nitroquinoline for various time intervals lead to induction of phosphorylation of Chk1 and H2AX. Induction was conducted in the presence or absence of VE-821 or KU55933+NU7441. VE-821 inhibited Chk1 phosphorylation by >70% for up to 3 hr but inhibition of H2AX phosphorylation declined from 70% at 1 hr to 40% at 3 hr. NU7441+KU55933 inhibited both Chk1 and H2AX phosphorylation in a time-dependent manner indicating increased dependence of the phosphorylation of ATM and DNA-PK. Accordingly, this indicates it is preferable to fix the cells or surrogate tissue within a 1-3 hour time frame depending on what marker is being utilized. In some embodiments, the cells or surrogate tissue should be fixed less than 1 hour after 4-nitroquinoline induction when γH2AX is being utilized as a biomarker. In other examples, the cells or surrogate tissue should be fixed less than 3 hour after 4-nitroquinoline induction when pChk1 is being utilized as the biomarker.

x) Evaluation of UV Induced Phosphorylation of Chk1 and γH2AX Over Various Time Intervals Following Treatment with Inhibitors of ATR, DNA-PK, and/or ATM Coverslips were sterilised in methanol and placed in the bottom of a 6-well culture dish. 2×10$^5$ MCF7 cells were seeded into each well of a 6-well culture dish in culture medium (RPMI-1640 with 10% FBS and 1% penicillin and streptomycin) and allowed to adhere for 24 hours. Medium was replaced by fresh medium containing compound VE-821 (10 µM) and incubated at 37° C. for 15 minutes where appropriate. Cells were exposed to 20 J/m$^2$ UV using a Stratalinker-2400 (Stratagene). Cells were incubated at 37° C. for 0.5, 1 and 3 hours at which points they were washed with 2 mls PBS and fixed. Cells were fixed using 4% (w/v) paraformaldehyde for 20 minutes at room temperature and permeablised using 0.5% (v/v) Triton-X-100 for 30 minutes at room temperature. Permeablised cells were blocked using 10% (v/v) goat serum and 5% (w/v) BSA in PBS for 1 hour at room temperature, the coverslips removed and subjected to immunofluorescent analysis using primary antibodies diluted in 1% (w/v) BSA in PBS at 4° C. overnight: rabbit anti-pChk1$^{Ser345}$ (133D3, Cell Signaling Technology, 1:300) and mouse anti-phospho-Histone H2AX$^{Ser139}$ (JBW301, Millipore, 1:1000). These were detected using the appropriate secondary antibodies diluted in 1% (w/v) BSA in PBS for 1 hour at room temperature protected from light: anti-rabbit AlexaFluor 546 (Invitrogen, 1:1000) or anti-mouse AlexaFluor 546 (Invitrogen, 1:1000). Coverslips were washed three times for 10 minutes in PBS after incubation with each antibody. DNA was stained using Vectashield with DAPI (Vector Laboratories). Images were captured using a Zeiss LSM 700 confocal microscope (Zeiss) with Zen 2009 software (Zeiss) using and ×40 lens and wavelengths of 405 nm and 561 nm. Mean nuclear fluorescence for at least 50 nuclei was measured using ImageJ software (National Institutes of Health, USA) and the data analysed using GraphPad Prism software version 6.0.

Figure 12:
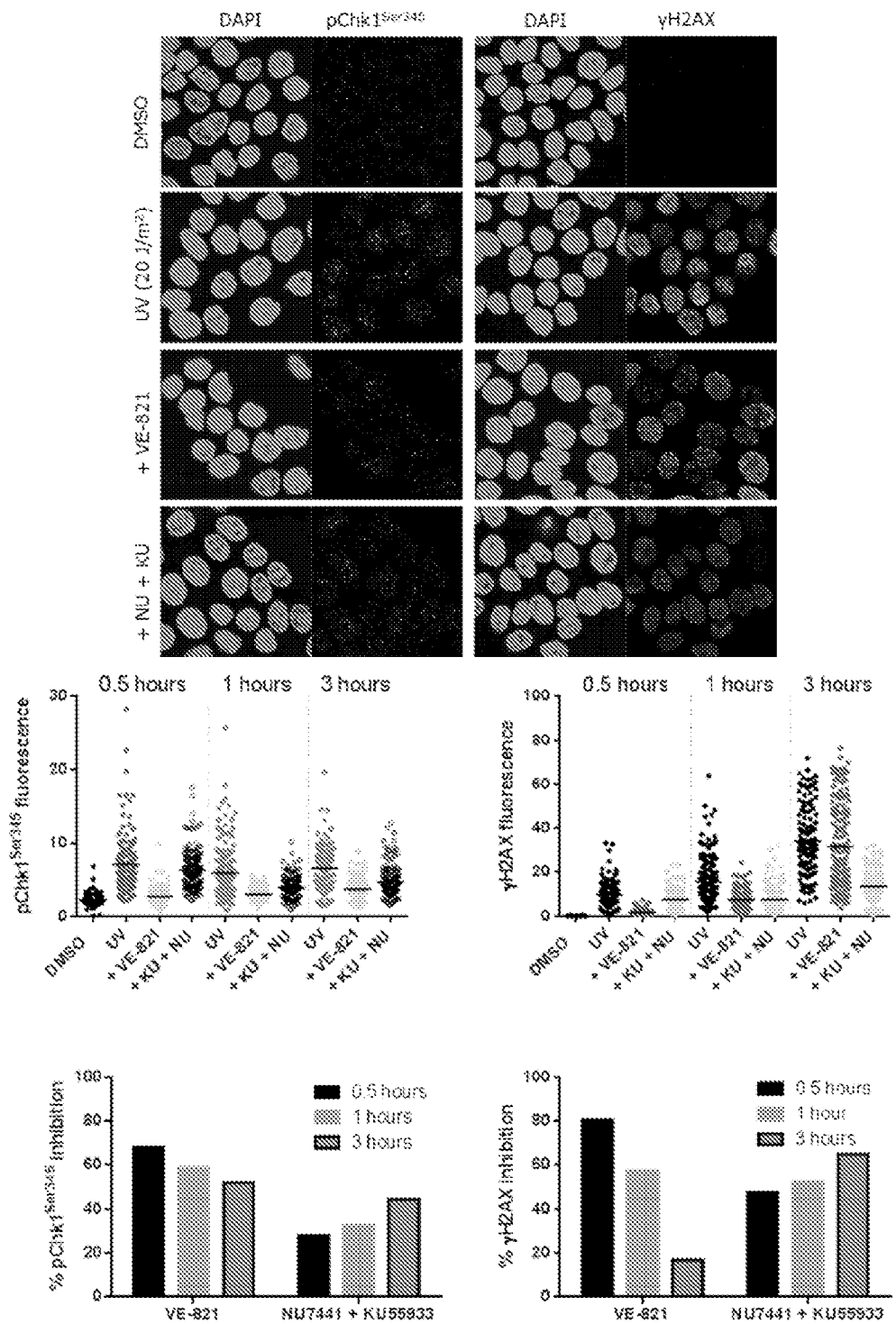
FIG. 12 depicts the levels of $pChk1^{Ser345}$ and γH2AX in MCF7 cells treated with UV and VE-821 or KU55933 and NU7441 for varying time intervals using immunofluorescence.

As shown in FIG. 12, treatment of MCF7 cells with UV for various time intervals lead to induction of phosphorylation of Chk1 and H2AX. Induction was conducted in the presence or absence of VE-821 or KU55933+NU7441. VE-821 inhibition decreased from 70% at 0.5 hr to 55% at 3 hr, with a corresponding increase in inhibition by ATM inhibitor NU7441 and DNA-PK inhibitor KU55933 from 30-50% over the same time frame. This indicates that at later time points phosphorylation is also dependent on DNA-PK and ATM.

Inhibition of γH2AX by VE-821 declined from 80% at 0.5 hr to <20% at 3 hr, while inhibition by NU7441 and KU55933 increased from 50-60% within that same time frame suggesting that at 3 hr most of the phosphorylation of H2AX was due to DNA-PK and ATM. Accordingly, a similar result was achieved when using UV to induce the cells. As with 4-nitroquinline induction, it is preferable to fix the cells or surrogate tissue within a 1-3 hour time frame depending on what marker is being utilized. In some embodiments, the cells or surrogate tissue should be fixed less than 1 hour after UV induction when γH2AX is being measured. In other examples, the cells or surrogate tissue should be fixed less than 3 hour after UV induction when pChk1$^{Ser345}$ is being measured.

xi) Evaluation of Rabbit Anti-pChk1$^{Ser345}$ Antibody for Use in Immunofluorescence Assay Coverslips were sterilised in methanol and placed in the bottom of a 6-well culture dish. $2\times10^5$ MCF7 cells were seeded into each well of a 6-well culture dish in culture medium (RPMI-1640 with 10% FBS and 1% penicillin and streptomycin) and allowed to adhere for 24 hours. Medium was replaced by fresh medium containing 4-nitroquinoline (2.5 μM) where appropriate and incubated at 37° C. for 2 hours. Cells were washed in PBS, fixed using 4% (w/v) paraformaldehyde for 20 minutes at room temperature and permeablised using 0.5% (v/v) Triton-X-100 for 30 minutes at room temperature. Permeablised cells were blocked using 10% (v/v) goat serum and 5% (w/v) BSA in PBS for 1 hour, the coverslips removed and subjected to immunofluorescent analysis rabbit anti-pChk1$^{Ser345}$ diluted in 1% (w/v) BSA in PBS (133D3, Cell Signaling Technology, 1:50, 1:150 or 1:300) overnight at 4° C. and the secondary anti-rabbit AlexaFluor 546 (Invitrogen, 1:1000 in 1% (w/v) BSA in PBS) for 1 hour at room temperature protected from light. Coverslips were washed three times for 10 minutes in PBS between antibodies. DNA was stained using Vectashield with DAPI (Vector Laboratories). Images were captured using a Zeiss LSM 700 confocal microscope (Zeiss) with Zen 2009 software (Zeiss) using and ×40 lens and wavelengths of 405 nm and 561 nm. Mean nuclear fluorescence for at least 50 nuclei was measured using Image) software (National Institutes of Health, USA) and the data analysed using GraphPad Prism software version 6.0.

Figure 13:
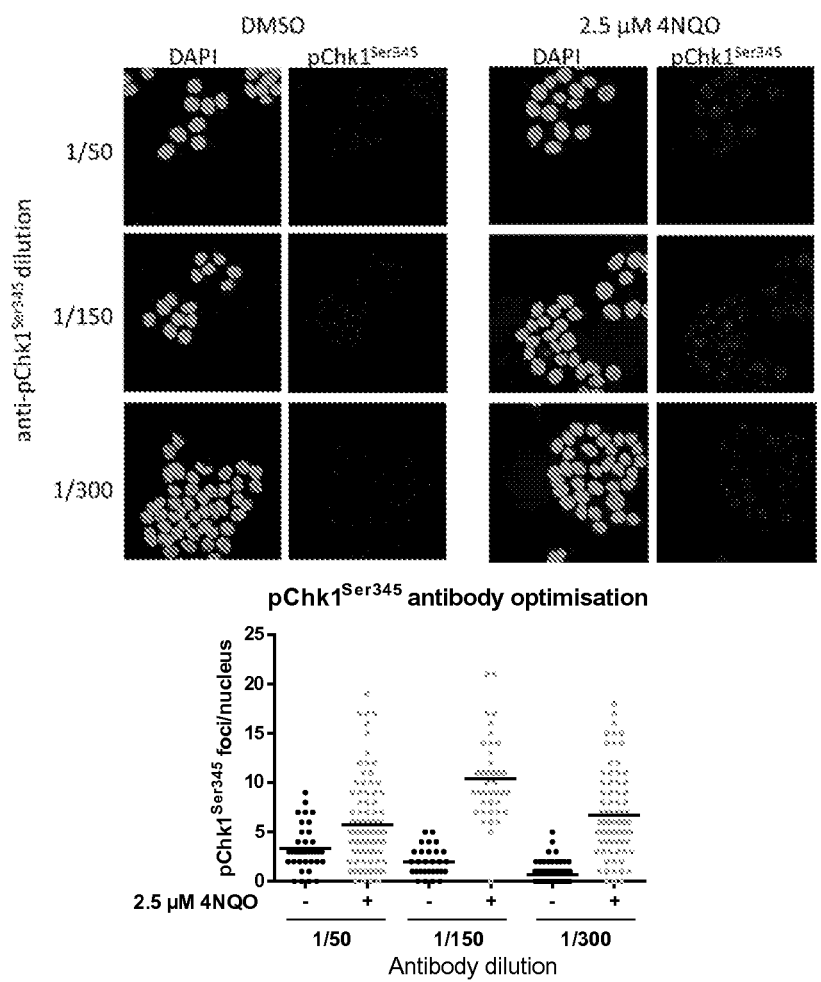
FIG. 13 depicts immunofluorescence of 4-nitroquinoline induced $pChk1^{Ser345}$ in MCF7 cells at varying dilutions of the anti-$pChk1^{Ser345}$ antibody.

As shown in FIG. 13, the 1:300 dilution of the pChk1$^{Ser345}$ antibody provided optimal sensitivity using immunofluorescence. However, other antibody dilutions also showed varying degrees of detection sensitivity.

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:

1. A method for monitoring DNA damage in a subject by measuring accumulation of γH2AX from blood, the method comprising:
    a) treating a subject with an ATR inhibitor;
    b) taking blood samples from the subject at various intervals;
    c) treating the blood samples with a DNA damaging agent;
    d) isolating white blood cells from the blood samples; and
    e) measuring γH2AX levels in the white blood cells by using antibodies specific for γH2AX.

2. The method of claim 1, wherein the DNA damaging agent is 4-nitroquinoline.

3. The method of claim 1, wherein the white blood cells are purified by simultaneously fixing the blood sample and lysing red blood cells within the blood sample, followed by centrifugation.

4. The method of claim 1, wherein the measurement of γH2AX levels is done by flow cytometry.

5. The method of claim 1, wherein the measurement of γH2AX levels is performed in CD3+ white blood cells.

* * * * *